United States Patent [19]

Willock

[11] 4,172,033
[45] Oct. 23, 1979

[54] ARTIFICIAL KIDNEY PROPORTIONING SYSTEM

[75] Inventor: Charles B. Willock, Milwaukie, Oreg.

[73] Assignee: DWS, Inc., Portland, Oreg.

[21] Appl. No.: 841,990

[22] Filed: Oct. 13, 1977

Related U.S. Application Data

[63] Continuation of Ser. No. 675,078, Apr. 8, 1976, abandoned, which is a continuation of Ser. No. 535,305, Dec. 23, 1974, abandoned.

[51] Int. Cl.² ........................................... B01D 31/00
[52] U.S. Cl. ........................................ 210/91; 210/85; 210/321 B
[58] Field of Search ................. 210/22, 87, 90, 96 M, 210/321 B, 91, 85

[56] References Cited

U.S. PATENT DOCUMENTS

| | | | |
|---|---|---|---|
| 3,598,727 | 8/1971 | Willock | 210/22 |
| 3,669,880 | 6/1972 | Marantz et al. | 210/22 |
| 3,844,940 | 10/1974 | Kopf et al. | 210/22 |
| 3,946,731 | 3/1976 | Lichtenstein | 210/87 |
| 3,990,973 | 11/1976 | Boag et al. | 210/87 |
| 4,021,341 | 5/1977 | Cosentino et al. | 210/87 |

Primary Examiner—Frank A. Spear, Jr.
Attorney, Agent, or Firm—Klarquist, Sparkman, Campbell, Leigh, Hall & Whinston

[57] ABSTRACT

An artificial kidney dialysate system provides a predetermined rate of flow of dialysate solution into a dialyzer, and a predetermined rate of flow of dialysate solution from the outlet of the dialyzer. Through positive displacement pumping at the inlet and outlet of the dialyzer, the two rates can be adjusted so that an accurately predetermined quantity of excess fluid from the patient's blood stream can be withdrawn into the dialysate solution.

2 Claims, 2 Drawing Figures

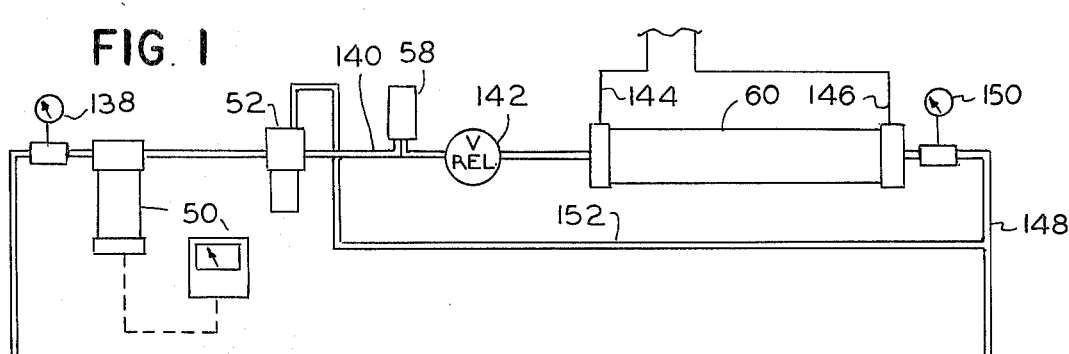
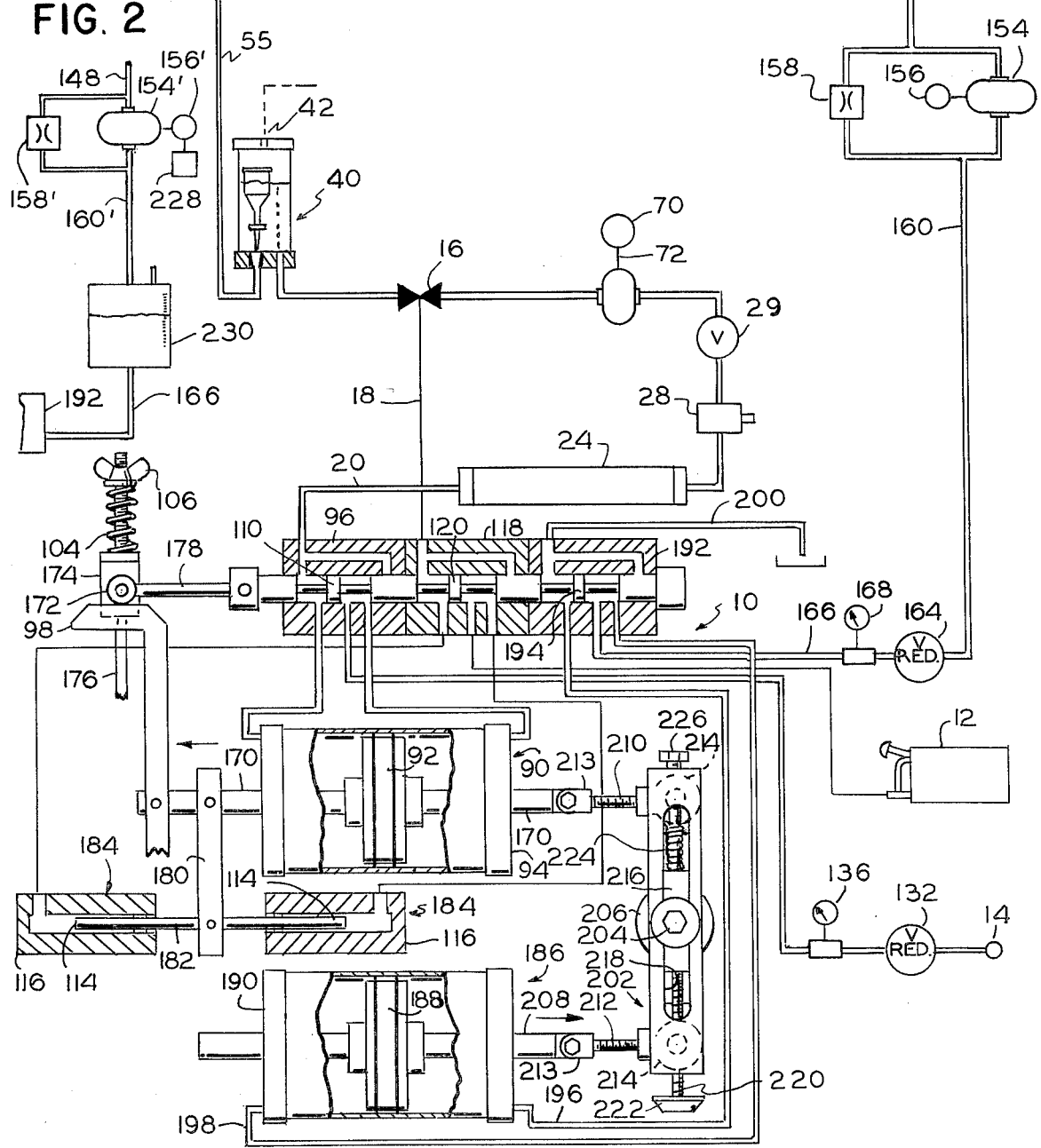

ARTIFICIAL KIDNEY PROPORTIONING SYSTEM

This is a continuation of my application Ser. No. 675,078, filed Apr. 8, 1976, which is a continuation of application Ser. No. 535,305, filed Dec. 23, 1974 (both now abandoned).

BACKGROUND OF THE INVENTION

This invention relates to an artificial kidney system and particularly to such a system wherein patient fluid exchange can be regulated.

A conventional artificial kidney machine includes a dialyzer receiving a dialysate solution, comprising a mixture of dialysate concentrate and water, into which impurities in the patient's blood pass as the dialysate solution flows through the dialyzer. A negative pressure may be applied at the outlet of the dialyzer for withdrawing the used dialysate solution with impurities, collectively known as diffusate. Such negative pressure means may comprise a venturi supplied with pumping water for aspirating the diffusate. By increasing the negative pressure, it is possible to remove more solution from the dialyzer than would conventionally be accounted for by the dialysate solution supplied and the addition of impurities. While excessive negative pressure might rupture the dialyzer membrane and withdraw blood into the dialysate solution, it is possible by application of a lesser negative pressure to reduce the quantity of undesired liquids accumulated by the patient. The application of the negative pressure value may be rather critical and the quantity of fluid removed from the patient is not easily predetermined.

SUMMARY OF THE INVENTION

According to the present invention, an artificial kidney system includes first apportioning means for providing at least a substantial part of the dialysate solution for a dialyzer, and second apportioning means for receiving dialysate solution from the dialyzer. Means coordinate the operation of the second apportioning means with the first apportioning means for predetermining the ratio of dialysate solution passing in and out of the dialyzer. In a particular embodiment, the apportioning means comprise first and second pumps which are interconnected so that a predetermined pumping rate is established in the dialysate outlet pump as compared with the dialysate pump which provides the solution to the dialyzer. A negative pressure means and a pressure reducer are disposed in that order between the dialyzer and the second pump for providing a predetermined constant pressure to the input of the second pump while sufficient negative pressure is applied to the dialyzer for supplying just the quantity of dialysate solution demanded by the second pump. The negative pressure means suitably comprises a pumping device and a bypass connected thereacross. According to the ratio of pumping rates selected for the said first and second pumps, the amount of fluid withdrawn from, or even added to, the patient can be accurately predetermined.

It is an object of the present invention to provide an improved artificial kidney system which can be accurately controlled in its operation.

It is another object of the present invention to provide an improved artificial kidney system wherein fluid flow between the patient's blood stream and the dialysate solution can be accurately predetermined.

It is another object of the present invention to provide an improved artificial kidney system for withdrawing a predetermined fluid quantity from a patient while accomplishing dialysis.

The subject matter which I regard as my invention is particularly pointed out and distinctly claimed in the concluding portion of this specification. The invention, however, both as to organization and method of operation, together with further advantages and objects thereof, may best be understood by reference to the following description taken in connection with the accompanying drawings wherein like reference characters refer to like elements.

DRAWINGS

FIG. 1 is a diagrammatic view of an artificial kidney system forming one embodiment of the present invention; and FIG. 2 is a partial diagrammatic view of an artificial kidney system according to another embodiment of the present invention.

DETAILED DESCRIPTION

Referring to the drawings and particularly to FIG. 1, a system according to the present invention includes dialysate apportioning apparatus 10 for pumping dialysate concentrate liquid from a concentrate container 12 and tap water from a tap water supply 14. The dialysate concentrate liquid is fed to a mixing venturi 16 through a line 18, and the tap water is fed to the mixing venturi through a line 20, heater 24, a temperature control 28, a reducing valve 29 and a negative pressure device 72, the latter comprising a positive displacement pump such as a gear pump driven by motor 70. The negative pressure device tends to pump the heated water faster than the water is supplied from apparatus 10. This establishes a negative pressure or partial vacuum in the water approaching such negative pressure device to cause a fraction of the air in this portion of the water to concentrate into bubbles which remain in the water as the dialysate concentrate liquid and the water are mixed together by venturi 16 to form a dialysate solution. The solution passes through a float type deaerator or bubble trap 40 which causes the air bubbles to escape through a vent 42 leaving finely dispersed air in the solution in a precise concentration. The apparatus as employed for removing air in this manner is more fully set forth in my U.S. Pat. No. 3,598,727 granted Aug. 10, 1971.

The solution from deaerator 40 passes through a line 55 where the temperature is measured by dialysate temperature gauge 138, to salinity detector 50, and from there to solenoid operated bypass valve 52 from which the solution is normally directed to line 140. The solution in line 140 passes through flow gauge 58 and relief valve 142 to the dialysate input connection of dialyzer 60. The dialyzer 60 is further provided with lines 144 and 146 by means of which the blood of the patient is circulated through the dialyzer whereby the dialyzer solution removes wastes from the blood. The dialyzer includes a dialysate outlet which is connected to outlet line 148 into which the waste-carrying dialysate solution or diffusate is discharged. Line 148 is provided with a negative pressure gauge 150. Also, bypass line 152 is coupled from an alternate output of bypass valve 52 to the outlet line 148 whereby the dialyzer can be controllably shunted out of the system if so desired.

Outlet line 148 is further coupled to the inlet of a negative pressure pump 154, which may comprise a positive displacement gear pump, such as disclosed in my aforementioned U.S. Pat. No. 3,598,727, driven by motor 156. Pump 154 applies a negative pressure at the outlet of the dialyzer for withdrawing the dialysate solution therefrom thereby causing the dialysate solution to pass through the dialyzer. Negative pressure pump 154 is shunted by a restrictive orifice which may take the form of a manually adjustable reducing valve 158. Valve 158 provides a bypass connected across negative pressure pump 154 whereby the negative pressure produced in line 148 can be decreased in accordance with the pressure encountered in line 160 at the outlet of pump 154.

Line 160 is connected to pressure reducer 164 which provides a constant predetermined pressure of dialysate solution in line 166. Pressure gauge 168 is connected to this line. In the typical case, the pressure in line 166 is selected to fall in the range of from 150 mm of mercury to 300 mm of mercury, in accordance with the manual setting of pressure reducer 164.

Apportioning apparatus 10 includes a double acting, positive displacement pump 90 having a piston 92 driven by the pressure of the tap water, via pressure reducer 132, alternately in opposite directions to pump the tap water alternately from opposite ends of pump cylinder 94 through a four-way spool valve 96 to the line 20. The valve 96 also controls the supply of the tap water alternately to opposite ends of the cylinder to drive the piston and refill each end of the cylinder. Pressure reducer 132 keeps the water pressure on the outlet side thereof connected to valve 96 at a substantially constant predetermined pressure, e.g. 20 pounds per square inch.

The valve 96 is alternately reversed by cam actuator 98 connected to rod 170 which is secured to piston 92. A follower roller 172 carried by block 174 connected to a rod 176 is urged downwardly by a spring 104 which is adjustable in compression by wing nut 106 on the rod 176, while a link 178 connects follower 172 to the spool 110 of valve 96. The follower drops as it encounters each end of cam actuator 98, when piston 92 reaches the ends of its stroke. Link 178 is then forced in an opposite direction, causing valve 96 to deliver water to cylinder 94 for reversing the direction of movement of piston 92.

Also connected to piston rod 170 is a link 180 attached to a rod 182 which at ends thereof forms a pair of pistons or rams 114 cooperating with cylinders 116 for providing positive displacement pumps 184 to pump the dialysate concentrate liquid through four-way spool valve 118 and to the line 18 for supplying a flow of concentrate which is a fixed fraction of the supply of water pumped by pump 90. Spool 120 of valve 118, connected to spool 110 and also driven in response to reciprocation of link 178, alternately directs dialysate concentrate to each of the pumps 184, and receives dialysate concentrate therefrom for supplying line 18, wherein a given pump 184 supplies concentrate while the other receives concentrate. The apportioning apparatus as above described is also as set forth in my U.S. Pat. No. 3,598,727 granted Aug. 10, 1971.

A second positive displacement pump 186 including a piston 188 received within a cylinder 190 is provided in accordance with the present invention, and is suitably similar in its dimensions and pumping capacity to pump 90. Opposite ends of cylinder 190 alternately receive the dialysate solution discharged from line 166 by way of four-way spool valve 192 provided with spool 194 connected to and operated conjointly with spools 120 and 110 by movement of link 178. Line 166 is connected to the center port of spool valve 192 alternately coupled to lines 196 and 198 by action of the valve. Lines 196 and 198 lead to ends of cylinder 190. As one end of cylinder 190 receives used dialysate solution, the dialysate solution on the opposite side of piston 188 therefrom is forced through the connecting line to valve 192 where the used dialysate solution is finally coupled via one of the end discharge ports of the valve to drain line 200.

Piston rod 208 of pump 186 is driven via the reciprocating movement of piston rod 170 of pump 90 through intervening pivotable lever 202. Lever 202 pivots about a support bolt 204 threadably received into a base 206. The ends of the lever 202 are respectively pivotally connected to piston rods 170 and 208 by means of threaded rods 210 and 212 supplied with clevis connections 213 at first ends thereof coupled to the aforementioned piston rods, and eye connections 214 through which pass the shanks of bolts secured to the underside of lever 202 at either end thereof. Center block 216, through which bolt 204 passes, is slidably received within elongated channel 218, and a threaded control rod 220 provided with an end operating knob 222 is received through a threaded bore in one end of lever 202, for passing axially along channel 218 in end contacting relation with block 216. The remaining end of block 216 is abutted by a spring 224 adjusted in compression by adjusting screw 226 threadably received through the opposite end of lever 202. Thus, as knob 222 is turned, lever 202 is moved longitudinally with respect to block 216 through the conjoint action of control rod 220 and the opposing bias of spring 224.

If the lever 202 is positioned thereby such that bolt 204 is located at the center of the lever, then piston 188 will execute the same length of stroke as piston 92. However, the lever 202 can be positioned axially in one direction or the other for affecting the ratio of movement of piston 188 relative to the movement of piston 92. The movement of piston 92 is brought about by the water pressure at the outlet of pressure reducer 132, and thus the movement of piston 92 is the independent factor, while movement of piston 188 is adjusted relative thereto. In a typical instance, the system constants are determined and valve 29 is adjusted such that pump 90 pumps at a rate of 500 milliliters per minute. Therefore, if lever 202 is centered upon bolt 204, pump 186 will pump at the same rate. Often, lever 202 is adjusted such that pump 186 operates at a greater rate, e.g. 508 milliliters per minute, as will hereinafter be more fully discussed.

Apportioning apparatus 10 operates in response to water pressure for supplying predetermined quantities of water and dialysate concentrate to mixing venturi 16, whereby dialysate solution is delivered to the input connection of dialyzer 60 at a first predetermined rate. The pressure in line 140 is substantially zero, but the dialysate solution is drawn through dialyzer 60 by the action of negative pressure pump 154. The used dialysate solution is delivered to pump 186 which transmits the used dialysate solution to drain tube 200 at a predetermined rate which may be the same as, or greater than or less than the rate of supply of dialysate solution to the dialyzer. Frequently, the physician will want to withdraw excess fluid or ultrafiltrate from the patient, whereby the rate of pump 186 is adjusted so that it is slightly greater than the pumping rate at which dialysate solution is delivered to the dialyzer. Consequently, the balance of liquid or ultrafiltrate is withdrawn through the dialyzer membrane from the blood stream of the patient.

The pressure reducer 164 supplies dialysate solution in line 166 for delivery to pump 186 at a predetermined, substantially constant pressure. Thus, in input line 160 of the pressure reducer, a positive pressure exists against which negative pressure pump 154 operates. The higher the back pressure in line 160, the more of the dialysate solution will be circulated around bypass valve 158, and the lower will be the negative pressure in line 148 for withdrawing dialysate solution from the dialyzer. As the back pressure in line 160 decreases, less dialysate solution passes through bypass valve 158 and the greater will be the negative pressure in line 148 for withdrawing dialysate solution from dialyzer 60 at a more rapid rate. The system is self-adjusting so that the quantity of dialysate solution is delivered through line 160 according to the demands of pump 186.

It is important to note that the pressure at the outlet of pressure reducer 164 and measured by gauge 168 is a predetermined constant value. By adjusting pressure reducer 164, the exact amount of dialysate solution withdrawn, and hence the liquid actually withdrawn from the patient, can be further adjusted. Thus, the pressure reducer 164 in a given instance is adjustable to provide an output pressure between 150 mm of mercury and 300 mm of mercury. For a nominal setting of pumping rate for pump 186 as determined by adjusting rod 220, an exact rate in the nature of a vernier adjustment can be provided through adjustment of pressure reducer 164. Ordinarily, adjusting rod 220 is preset, and the physician can convert the reading of gauge 168 to the equivalent pumping rate of pump 186. In the example cited, for pressure in line 166 in the range from 150 mm of mercury to 300 mm of mercury, the pumping rate of pump 186 varies in the range from 501 milliliters per minute to 510 milliliters per minute. The disirability of predetermining the pressure in line 166 for predetermined fluid withdrawal is therefore seen, since the pressure has an effect on the quantity of liquid pumped by pump 186. Negative pressure pump 154 together with bypass valve 158 works against the input pressure of pressure reducer 164 for supplying the correct withdrawing force at the output of the dialyzer to provide just the rate of flow then demanded by pump 186.

In summary, in regard to the FIG. 1 form of the invention, setting the knob 222 not only adjusts the rate of ultrafiltration, but also indicates such rate by virtue of its position. In addition, the position of the lever 202 relative to the bolt 204 also indicates the rate of ultrafiltration.

FIG. 2 illustrates an alternative embodiment according to the present invention wherein the quantity of fluid removed from the patient's blood stream can be monitored. In this system, manual control can be achieved by a conventional speed control means 228 for adjusting the speed of motor 156' which drives the positive displacement pump 154', e.g. a gear pump similar to pump 154 in FIG. 1. The outlet of pump 154' is delivered to head tank 230 via an intervening line 160', and the outlet of the head tank, i.e. at the bottom thereof, is provided to line 166 for connection to spool valve 192. Pump 154' may be shunted by adjustable bypass valve 158', in which case control 228 may be dispensed with. The FIG. 2 configuration is substituted for a portion of the FIG. 1 configuration between line 148 and line 166. The head tank 230 is desirably transparent and is provided with graduated markings therealong. Tank 230 supplies a nearly constant head for pump 186 by way of valve 192. The control 228 is adjusted, or valve 158' is adjusted, so that pump 154' causes a predetermined constant negative pressure to be exerted on line 148 from the dialyzer outlet whereby tank 230 is filled at the same rate dialysate solution is withdrawn therefrom, or at a greater rate or at a lesser rate. For example, the physician will frequently desire the dialysate solution to be withdrawn at a greater rate than supplied, for withdrawing excess fluid from the patient's blood stream. The pump 186 is adjusted by means of control rod 220 to have the same pumping rate for removal of dialysate solution as the rate at which dialysate solution is provided to the dialyzer. Control 228 is adjusted, or alternatively valve 158' is adjusted, so that the desired excess withdrawal is accomplished, as the same is observed in the head tank. The change in fluid level in the head tank 230 is then indicative of fluid or ultrafiltrate withdrawn from the patient.

While I have shown and described embodiments of my invention, it will be apparent to those skilled in the art that many changes and modifications may be made without departing from my invention in its broader aspects. I therefore intend the appended claims to cover all such changes and modifications as fall within the true spirit and scope of my invention.

I claim:

1. An artificial kidney system comprising a dialyzer having an input and an output for dialyzing solution,
   pump means for supplying a dialyzing solution to and removing dialyzing solution and ultrafiltrate from said dialyzer at pressures to cause ultrafiltration at a range of desired rates,
   said pump means including a positive displacement piston and cylinder input pump and a positive displacement piston and cylinder output pump, each having a piston rod projecting from its cylinder,
   and means connected to said rods for indicating the rate of ultrafiltration.

2. An artificial kidney machine as recited in claim 1 in which the last named means adjusts the relative rates of operation of the two pumps.

* * * * *